(12) United States Patent
Tanaka

(10) Patent No.: US 8,602,969 B2
(45) Date of Patent: Dec. 10, 2013

(54) CAPSULE MEDICAL APPARATUS SYSTEM

(75) Inventor: Shinsuke Tanaka, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 480 days.

(21) Appl. No.: 12/838,745

(22) Filed: Jul. 19, 2010

(65) Prior Publication Data
US 2011/0034766 A1 Feb. 10, 2011

Related U.S. Application Data

(63) Continuation of application No. PCT/JP2010/051042, filed on Jan. 27, 2010.

(30) Foreign Application Priority Data

Jan. 28, 2009 (JP) .................................. 2009-017005

(51) Int. Cl.
*A61B 1/00* (2006.01)
*A61B 1/04* (2006.01)

(52) U.S. Cl.
USPC ............. 600/106; 600/101; 600/117; 600/118

(58) Field of Classification Search
USPC ........................... 600/106, 117, 118, 101, 170
See application file for complete search history.

(56) References Cited

U.S. PATENT DOCUMENTS

| 7,711,408 B2 * | 5/2010 | Uchiyama et al. | 600/424 |
| 7,946,979 B2 * | 5/2011 | Gilad et al. | 600/109 |
| 2007/0299301 A1 * | 12/2007 | Uchiyama et al. | 600/101 |
| 2008/0294143 A1 | 11/2008 | Tanaka et al. | |
| 2009/0299142 A1 | 12/2009 | Uchiyama et al. | |

FOREIGN PATENT DOCUMENTS

| EP | 2 196 131 A1 | 6/2010 |
| JP | SHO 55-166142 | 12/1980 |
| JP | 2004-041709 | 2/2004 |
| JP | 2004-255174 | 9/2004 |
| JP | 2005-237979 | 9/2005 |
| JP | 2006-068501 | 3/2006 |
| WO | WO 2008/099851 A1 | 8/2008 |

OTHER PUBLICATIONS

European Search Report dated Jul. 2, 2012 from corresponding European Patent Application No. EP 10 73 5834.3.

* cited by examiner

*Primary Examiner* — Alireza Nia
(74) *Attorney, Agent, or Firm* — Scully, Scott, Murphy & Presser, P.C.

(57) ABSTRACT

A capsule medical apparatus system includes a rotating magnetic field generation apparatus that generates a desired rotating magnetic field in three-dimensional directions, a capsule medical apparatus that includes a magnet and a needle for puncture that can be projected and retracted in a rotation direction of the rotating magnetic field and is rotated in the direction of the rotating magnetic field when the rotating magnetic field is applied to the magnet, a step-out operation detecting unit that detects a step-out operation by which the capsule medical apparatus is inversely rotated when a luminal surface is punctured with the needle, and a magnetic-field control instructing unit that controls the rotating magnetic field generation apparatus on the basis of a detection result performed by the step-out operation detecting unit.

15 Claims, 15 Drawing Sheets

(PUNCTURED STATE)

CAPSULE ROTATING SPEED
(NORMAL SPEED)

CAPSULE ROTATING SPEED
(NORMAL SPEED)

CAPSULE ROTATING SPEED
(EXTREMELY-LOW SPEED)

CAPSULE MEDICAL APPARATUS SYSTEM

CROSS-REFERENCE TO RELATED APPLICATION

This application is a continuation of PCT international application Ser. No. PCT/JP2010/051042 filed on Jan. 27, 2010 which designates the United States, incorporated herein by reference.

BACKGROUND OF THE INVENTION

1. Field of the Invention

The present invention relates to a capsule medical apparatus system that can rotate a capsule medical apparatus introduced into a living body to puncture a desired luminal surface with a needle and inject liquid medicine into an affected part.

2. Description of the Related Art

In recent years, a swallowed capsule endoscope is developed in the field of an endoscope. The capsule endoscope has an imaging function and a radio function. Until the capsule endoscope is swallowed from the mouth of a patient for the sake of the observation of the inside of body cavity and then is naturally discharged from the human body, the capsule endoscope has, for example, a function for moving inside an organ such as an esophagus, a stomach, or a small intestine in accordance with the peristalsis and sequentially capturing images of the inside. In recent years, there is proposed, as such a capsule endoscope, a capsule endoscope that includes a needle that is connected to a liquid medicine tank and an actuator that projects the needle to be able to inject liquid medicine into a lesioned part or the like.

Japanese Laid-open Patent Publication No. 2004-255174 and Japanese Laid-open Patent Publication No. 2006-068501 disclose a device that detects a rotation state such as the deviance of the rotation of a capsule endoscope to the rotation of a rotating magnetic field on the basis of the change of the captured in-vivo images when applying a rotating magnetic field to the capsule endoscope to rotate the capsule endoscope and move the capsule endoscope.

SUMMARY OF THE INVENTION

A capsule medical apparatus system according to an aspect of the present invention includes a rotating magnetic field generation apparatus that generates a desired rotating magnetic field in three-dimensional directions; a capsule medical apparatus that is introduced into a living body, includes a magnet and a needle with which the capsule medical apparatus punctures a luminal surface by projecting and retracting the needle in a rotation direction of the rotating magnetic field, and rotates in a direction of the rotating magnetic field when the rotating magnetic field is applied to the magnet; a step-out operation detecting unit that detects, when the needle is diagonally projected toward the luminal surface to puncture the luminal surface, an step-out operation by which the capsule medical apparatus is inversely rotated at a rotating speed larger than a rotating speed of the rotating magnetic field after rotating the capsule medical apparatus to the rotation direction of the rotating magnetic field is stopped; and a magnetic-field control instructing unit that controls the rotating magnetic field generation apparatus on the basis of a detection result performed by the step-out operation detecting unit.

A capsule medical apparatus system according to another aspect of the present invention includes a rotating magnetic field generation apparatus that generates a desired rotating magnetic field in three-dimensional directions; a capsule medical apparatus that is introduced into a living body, includes a needle, with which the capsule medical apparatus punctures a luminal surface by projecting and retracting the needle in a rotation direction of the rotating magnetic field, and a magnet, and rotates in a direction of the rotating magnetic field when the rotating magnetic field is applied to the magnet; means for detecting, when the needle is diagonally projected toward the luminal surface to puncture the luminal surface, an step-out operation by which the capsule medical apparatus is inversely rotated at a rotating speed larger than a rotating speed of the rotating magnetic field after rotating the capsule medical apparatus to the rotation direction of the rotating magnetic field is stopped; and means for controlling the rotating magnetic field generation apparatus on the basis of a detection result of the step-out operation.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule medical apparatus system of the present invention will be explained in detail below with reference to the accompanying drawings. However, the present invention is not limited to these embodiments. Moreover, in the description of drawings, the same components have the same reference numbers.

First Embodiment

Figure 1:
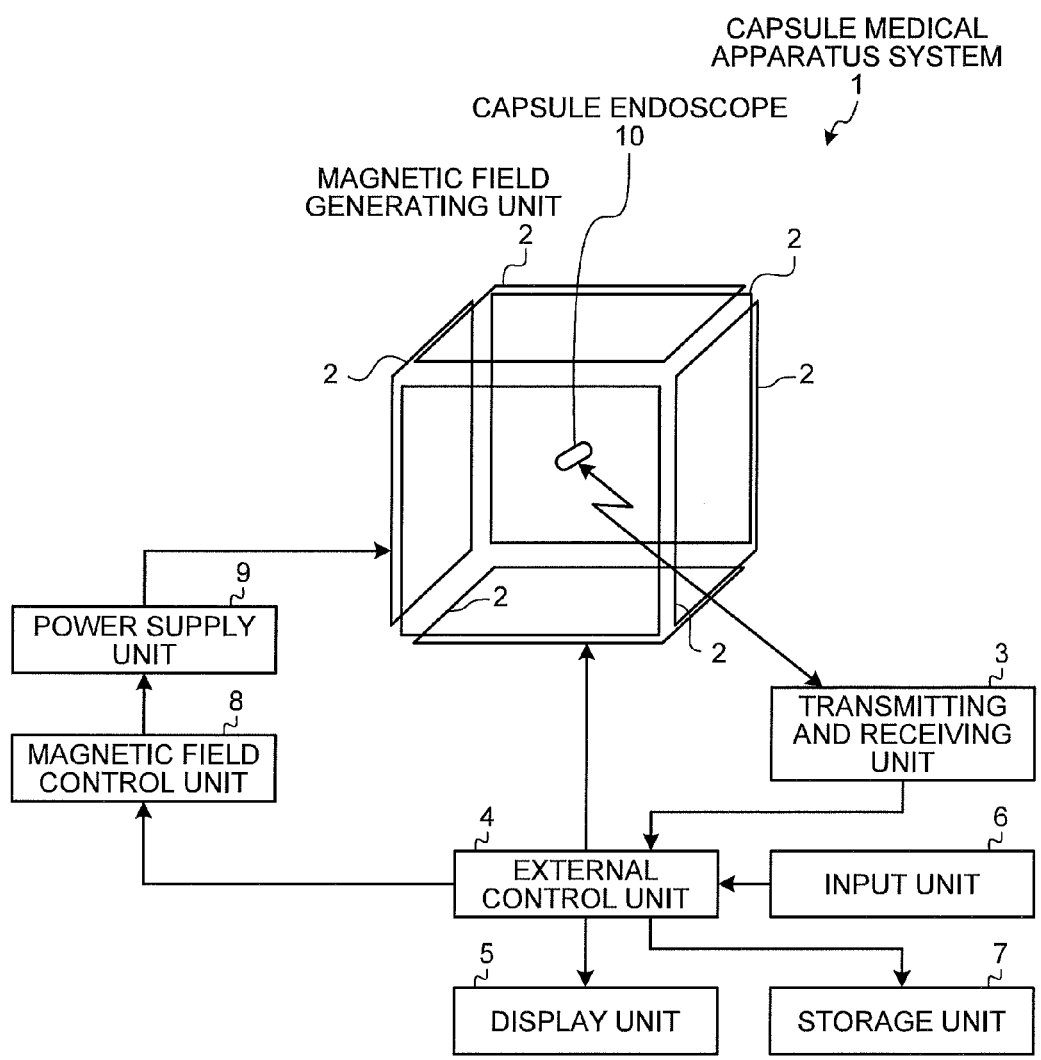
FIG. 1 is a pattern diagram illustrating the entire configuration of a capsule medical apparatus system according to a first embodiment of the present invention.

First, it will be explained about the first embodiment of the present invention. FIG. 1 is a pattern diagram illustrating the entire configuration of a capsule medical apparatus system 1 according to the first embodiment of the present invention. As illustrated in FIG. 1, the capsule medical apparatus system 1 according to the first embodiment includes a capsule endoscope 10 and a magnetic field generating unit 2. The capsule endoscope 10 is a capsule medical apparatus that is introduced into an intra-subject body cavity by being swallowed from the mouth of a subject and communicates with an external apparatus. The magnetic field generating unit 2 functions as a rotating magnetic field generation apparatus that is provided in the vicinity of the subject and can generate a desired rotating magnetic field in three-dimensional directions. Moreover, the capsule medical apparatus system 1 further includes a transmitting and receiving unit 3 and an external control unit 4. The transmitting and receiving unit 3 wirelessly communicates with the capsule endoscope 10 to receive a radio signal including an image captured by the capsule endoscope 10 and to transmit a manipulated signal to the capsule endoscope 10. The external control unit 4 controls each unit of the capsule medical apparatus system 1. Moreover, the capsule medical apparatus system 1 further includes a display unit 5 that displays the image captured by the capsule endoscope 10, an input unit 6 that inputs instruction information of indicating various types of operations of the capsule medical apparatus system 1 into the external control unit 4, and a storage unit 7 that stores image information captured by the capsule endoscope 10. Furthermore, the capsule medical apparatus system 1 includes a magnetic field control unit 8 that controls the generation of a magnetic field performed by the magnetic field generating unit 2 and a power supply unit 9 that supplies an electric power according to the control of the magnetic field control unit 8 to the magnetic field generating unit 2.

In this case, the transmitting and receiving unit 3 detects intra-subject position and posture of the capsule endoscope 10 on the basis of the reception field intensity of a signal transmitted from the capsule endoscope 10. The capsule medical apparatus system 1 may separately include a position detecting device that detects the position and posture of the capsule endoscope 10. For example, the capsule medical apparatus system 1 may provide a magnetic field generating unit or a magnetic field reflecting unit in the capsule endoscope 10, provide a plurality of magnetic field sensors to cover the periphery of the capsule endoscope 10 similarly to the magnetic field generating unit 2, and detect the position and posture of the capsule endoscope 10 on the basis of the detection result of the magnetic field sensors.

Figure 2:
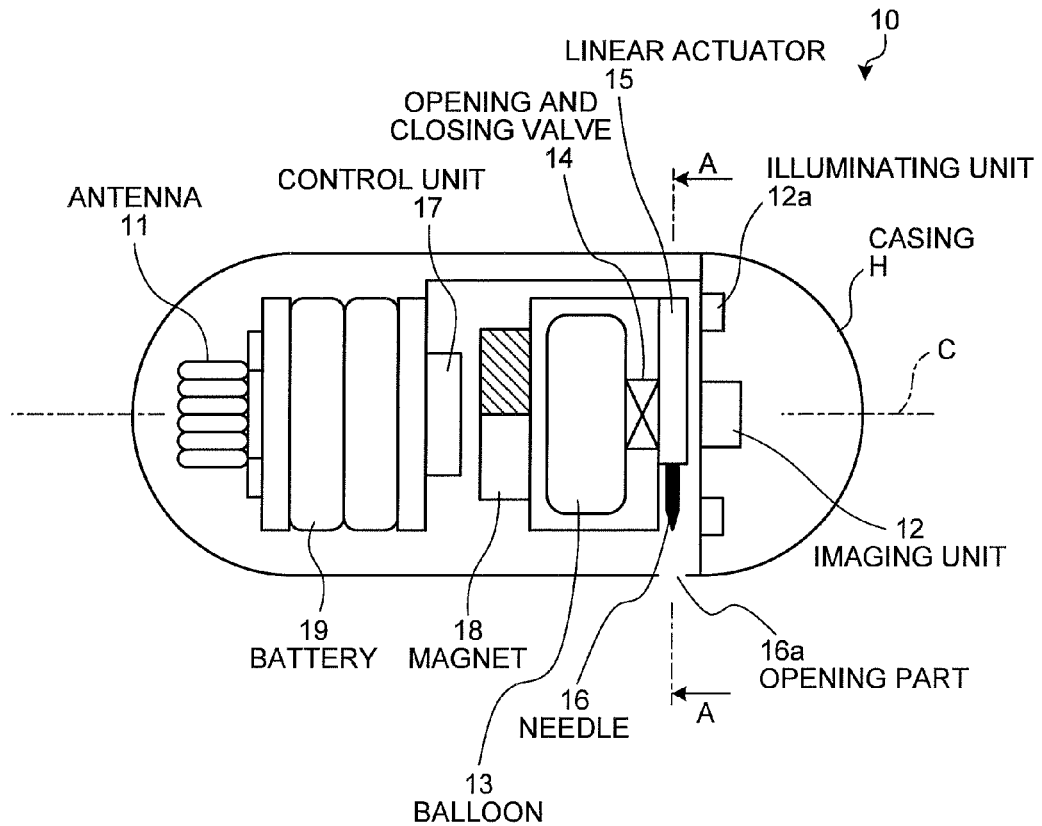
FIG. 2 is a pattern diagram illustrating the internal configuration of a capsule endoscope illustrated in FIG. 1.
Figure 3:
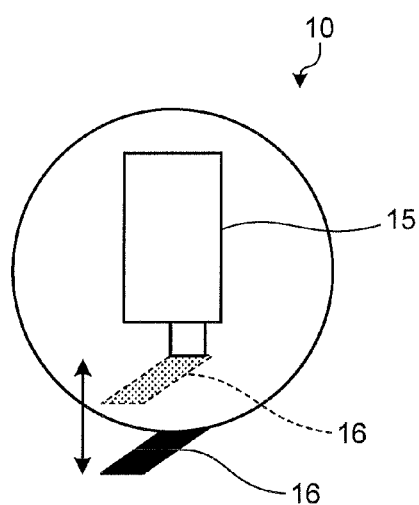
FIG. 3 is an A-A line sectional schematic view illustrating the projecting and retracting state of a needle of the capsule endoscope illustrated in FIG. 2.

Next, it will be explained about the capsule endoscope 10 illustrated in FIG. 1. FIG. 2 is a pattern diagram illustrating the internal configuration of the capsule endoscope 10 illustrated in FIG. 1. FIG. 3 is an A-A line sectional schematic view illustrating the projecting and retracting state of a needle. As illustrated in FIG. 2, the capsule endoscope 10 includes, in a casing H, an antenna 11 that transmits and receives a radio signal to and from the transmitting and receiving unit 3, an illuminating unit 12a that irradiates light to an observation view, and an imaging unit 12 that includes a lens for condensing reflected light and an imaging device for capturing the internal image of the body cavity of a subject. The imaging unit 12 functions as an image acquiring unit or an image acquiring means that sequentially acquires in-vivo images. Moreover, the capsule endoscope 10 further includes a balloon 13 and an opening and closing valve 14. The balloon 13 has a liquid-medicine tanking function for storing liquid medicine to be injected into an intra-subject affected part and a discharging function for generating the discharge pressure of liquid medicine by being formed of extensible film such as elastomer. The opening and closing valve 14 opens and closes the opening of the balloon 13 in accordance with the drive of a driving member not illustrated. Furthermore, the capsule endoscope 10 includes a linear actuator 15 and a needle 16. The linear actuator 15 has a motor or the like therein. The needle 16 is projected and retracted from and into the capsule endoscope 10 via an opening part 16a provided in the casing H and injects liquid medicine stored in the balloon 13 into an affected part near the luminal surface. Furthermore, the capsule endoscope 10 includes a control unit 17 that controls each component of the capsule endoscope 10 in accordance with the radio signal (manipulated signal) of the transmitting and receiving unit 3 received by the antenna 11, a discoid magnet 18 that generates a magnetic field in a radial direction, and a battery 19 that supplies an electric power to each component of the capsule endoscope 10.

The needle 16 can be projected and retracted from and into the surface of the casing H of the capsule endoscope 10. The magnetization direction of the magnet 18 is a radial direction. The magnet 18 is provided in the capsule endoscope 10 in such a manner that the center C of a long axis of the casing H constituting the capsule endoscope 10 and a magnetization direction of the magnet 18 are perpendicular to each other. Moreover, the leading end of the casing H near the imaging unit 12 of the capsule endoscope 10 is configured of a transparent member in such a manner that light by the illuminating unit 12a can irradiate an observation view.

The linear actuator 15 and the rear end of the needle 16 are connected to each other. As illustrated in FIG. 3, the needle 16 can be projected and retracted in a radial direction of the capsule endoscope 10 by using the linear actuator 15. Moreover, the needle 16 is inclined to the outside with respect to a tangent line of the casing H of the capsule endoscope 10 in the projected state in such a manner that the leading end is turned into the rotation direction around the center C of the long axis. The linear actuator 15 is controlled by the control unit 17.

Figure 4:
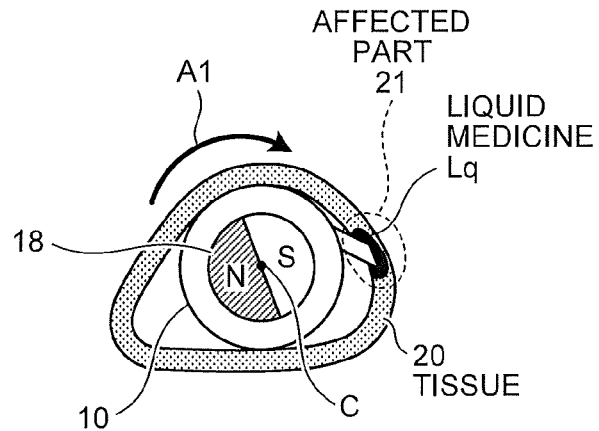
FIG. 4 is a cross-sectional view illustrating the punctured state of the needle and the injected state of liquid medicine of the capsule endoscope illustrated in FIG. 1.

In the capsule medical apparatus system 1, the capsule endoscope 10 is introduced into a living body (subject) that is a check target, and then in-vivo images acquired by the imaging unit 12 provided in the capsule endoscope 10 are observed by an operator such as a doctor outside the body. Then, the magnetic field control unit 8 controls an electric power to be supplied to the magnetic field generating unit 2 to change the magnetic field generated by the magnetic field generating unit 2 in accordance with the manipulation information input from the input unit 6 while the operator observes the in-vivo images, and thus the position and direction of the capsule endoscope 10 are controlled. When the capsule endoscope 10 arrives at the vicinity of an affected part, a manipulated signal by which the linear actuator 15 of the capsule endoscope 10 is driven is transmitted by the manipulation of the input unit 6, and thus the needle 16 is projected toward the outside of the capsule endoscope 10. As illustrated in FIG. 4, in a state where the needle 16 is projected, the capsule endoscope 10 punctures an affected part 21 of an tissue 20 with the needle 16 by generating a rotating magnetic field from the magnetic field generating unit 2 in such a manner that the capsule endoscope 10 is rotated around the center C of a long axis and in the inclined direction (A1 arrow direction) of the needle 16. Liquid medicine Lq can be then injected into the affected part 21 by opening the opening and closing valve 14.

Figure 5:
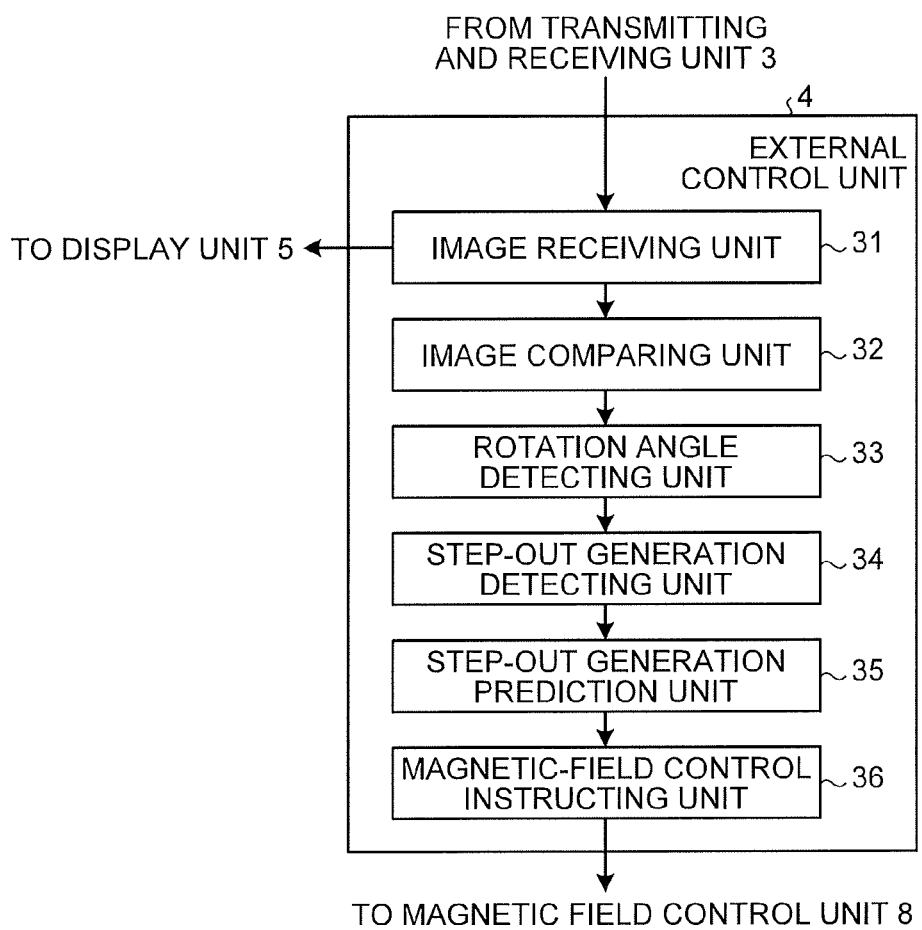
FIG. 5 is a block diagram illustrating the detailed configuration of an external control unit of the capsule medical apparatus system illustrated in FIG. 1.

In this case, as illustrated in FIG. 5, the external control unit 4 includes an image receiving unit 31, an image comparing unit 32, and a rotation angle detecting unit 33. The image receiving unit 31 sequentially acquires in-vivo images that are sequentially received by the transmitting and receiving unit 3. The image comparing unit 32 compares the adjacent in-vivo images received by the image receiving unit 31 in time series and extracts a characterizing portion that is common to the images. The rotation angle detecting unit 33 obtains a rotation angle of the capsule endoscope 10 from the inside-image position of the characterizing portion extracted from the image comparing unit 32. Furthermore, the external control unit 4 includes a step-out generation detecting unit 34 that detects the step-out operation of the capsule endoscope 10 caused by the deviance of rotation between the capsule endoscope 10 and an external rotating magnetic field on the basis of the rotation angle detected by the rotation angle detecting unit 33, and detects a step-out occurrence period from the time interval of the inverse rotation occurrence point of the capsule endoscope 10 in the step-out operation. Furthermore, the external control unit 4 includes a step-out generation prediction unit 35 and a magnetic-field control instructing unit 36. The step-out generation prediction unit 35 predicts an inverse rotation occurrence point of the capsule endoscope 10 in the next step-out operation on the basis of the detection result of the step-out operation performed by the step-out generation detecting unit 34. The magnetic-field control instructing unit 36 instructs the magnetic field control unit 8 to stop an external rotating magnetic field immediately before the next step-out operation occurrence point predicted by the step-out generation prediction unit 35.

The step-out generation detecting unit 34 functions as a step-out operation detecting unit or a step-out operation detecting means, which detects the step-out operation of the capsule endoscope 10. The step-out generation prediction unit 35 functions as a step-out predicting unit or a step-out predicting means that predicts the step-out operation of the capsule endoscope 10. The magnetic-field control instructing unit 36 functions as a magnetic field control means that controls a rotating magnetic field generation apparatus before the inverse rotation of the capsule endoscope 10 in the step-out operation on the basis of the detection result performed by the step-out operation detecting unit or the step-out operation detecting means. The magnetic-field control instructing unit 36 instructs the magnetic field control unit 8 to stop the external rotating magnetic field immediately before the inverse rotation occurrence point of the capsule endoscope 10 in the next step-out operation. Therefore, the punctured state of the needle can be certainly maintained without the inverse rotation of the capsule endoscope 10.

Figure 6:
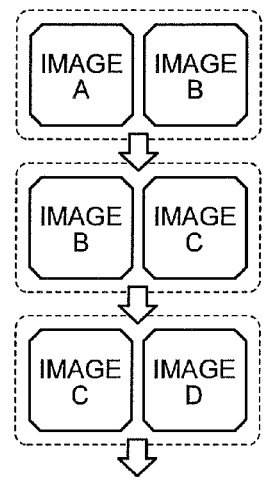
FIG. 6 is a pattern diagram illustrating an example of an image comparison that is performed by an image comparing unit of the capsule medical apparatus system illustrated in FIG. 1.
Figure 7:
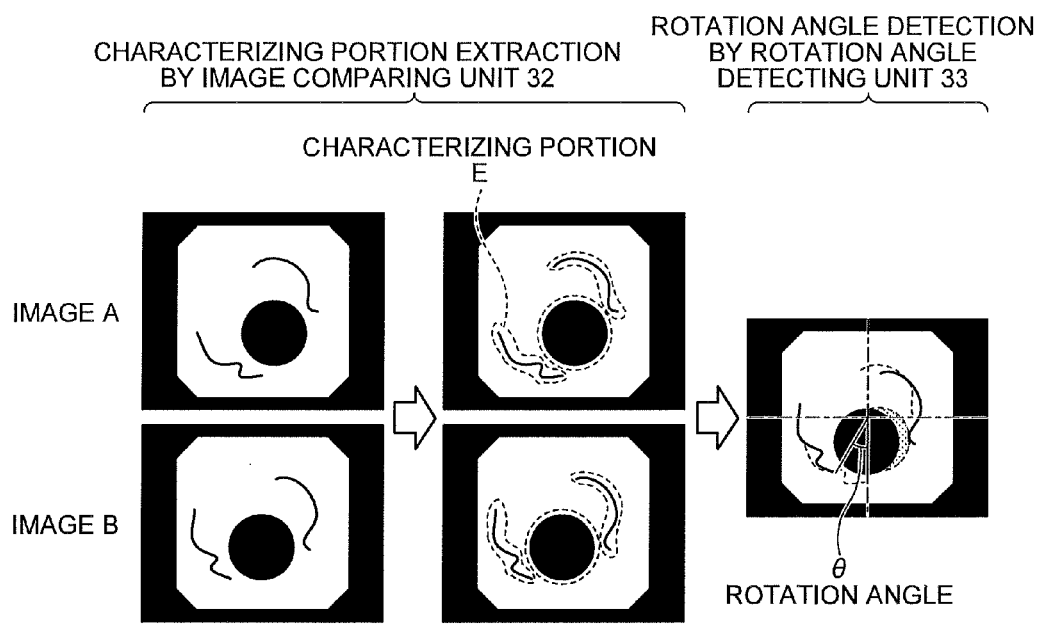
FIG. 7 is a diagram illustrating an example of a rotation angle detection that is performed by a rotation angle detecting unit of the capsule medical apparatus system illustrated in FIG. 1.

The image comparing unit 32 compares, as described above, two adjacent in-vivo images in time series among the sequentially-received in-vivo images. For example, when images "A"→"B"→"C"→"D" are input in time series, the images "A" and "B" are compared, then the images "B" and "C" are compared, and then the images "C" and "D" are compared, as illustrated in FIG. 6. In this case, the images "B", "C", "D", and the like that have been compared once are stored in a temporary storage unit not illustrated, and are read in the next comparison process. As illustrated in FIG. 7, the image comparing unit 32 extracts a characterizing portion E of the images "A" and "B".

For example, as illustrated in FIG. 7, the rotation angle detecting unit 33 superimposes the compared two images "A" and "B" and detects the rotation angle θ of the image B, that is, the rotation angle θ of the capsule endoscope 10 from the difference between positions on the images A and B of the characterizing portion E extracted by the image comparing unit 32. The rotation angle detecting unit 33 functions as a rotation angle detecting means that detects the rotation angle of the capsule endoscope 10.

Figure 8:
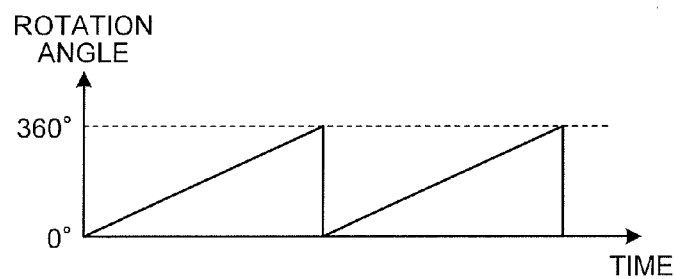
FIG. 8 is a diagram illustrating the time change of a rotation angle when the rotation of the capsule endoscope and the rotation of external rotation magnetization are synchronized with each other without the step-out of the capsule endoscope in the capsule medical apparatus system illustrated in FIG. 1.

In this case, when the capsule endoscope 10 is rotated, the captured in-vivo images continue to be rotated. If the capsule endoscope 10 is rotated at a constant rotating speed and in-vivo images are captured at a constant frame rate, a rotation angle detected by the rotation angle detecting unit 33 has a constant value and the rotation angle is changed in proportion to the time as illustrated in FIG. 8.

Figure 9A:
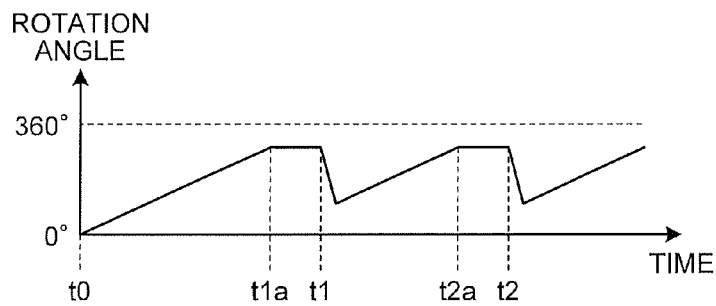
FIG. 9A is a diagram illustrating the time change of a rotating speed when the step-out of the capsule endoscope occurs in the capsule medical apparatus system illustrated in FIG. 1.
Figure 9B:
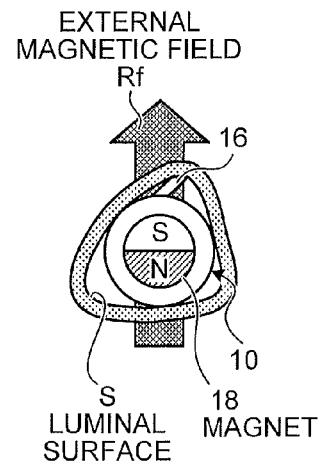
FIG. 9B is a diagram illustrating a state when a rotating magnetic field is applied to the capsule endoscope at a time point t0 illustrated in FIG. 9A.
Figure 9C:
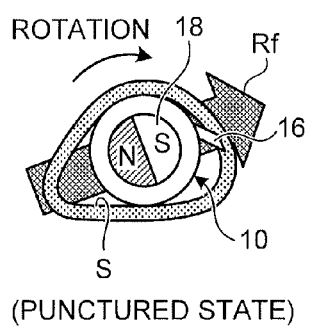
FIG. 9C is a diagram illustrating a state when the capsule endoscope is rotated in synchronization with the rotating magnetic field applied from the time point t0 illustrated in FIG. 9A.
Figure 9D:
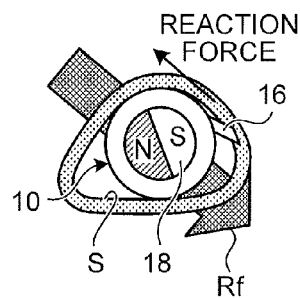
FIG. 9D is a diagram illustrating a state when the rotation of the capsule endoscope is stopped at a time point t1a illustrated in FIG. 9A.
Figure 9E:
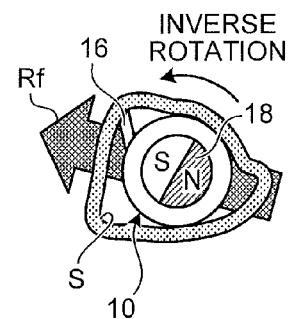
FIG. 9E is a diagram illustrating a state when the needle is removed from a luminal surface by starting the inverse rotation of the capsule endoscope at a time point t1 illustrated in FIG. 9A.

However, when there is a step-out operation, the temporal change of a rotation angle of the capsule endoscope 10 does not reach 360° as illustrated in FIG. 9A. In other words, the capsule endoscope 10 does not rotate by one revolution and inversely rotates at a time point. As illustrated in FIG. 9B, the capsule endoscope 10 is first applies with an external magnetic field (rotating magnetic field) Rf that is rotating from a time point t0 illustrated in FIG. 9A in a state where the needle 16 is projected. Then, the capsule endoscope 10 rotates in synchronization with the rotation of the rotating magnetic field Rf from the time point t0 (FIG. 9C). Next, as time is close to a time point t1a illustrated in FIG. 9A, the rotation of the capsule endoscope 10 is delayed from the rotation of the rotating magnetic field Rf due to the reaction force of the luminal surface, and thus the rotation of the capsule endoscope 10 is stopped at the time point t1a illustrated in FIG. 9A (FIG. 9D). After that, when the rotation of the rotating magnetic field Rf is continued in a state where the rotation of the capsule endoscope 10 is stopped, the capsule endoscope 10 suddenly starts inverse rotation at a time point t1 illustrated in FIG. 9A. As a result, the needle 16 is removed from the luminal surface S (FIG. 9E). Then, when the rotation of the rotating magnetic field Rf is further continued, the capsule endoscope 10 is rotated again in synchronization with the rotation of the rotating magnetic field Rf.

The step-out generation detecting unit 34 particularly detects inverse rotation occurrence points t1 ad t2 from the change of a rotation angle of the capsule endoscope 10 illustrated in FIGS. 9A to 9E. Preferably, the step-out generation detecting unit 34 detects rotation stop points t1a and t2a at which the rotation of the capsule endoscope 10 is stopped.

Figure 10:
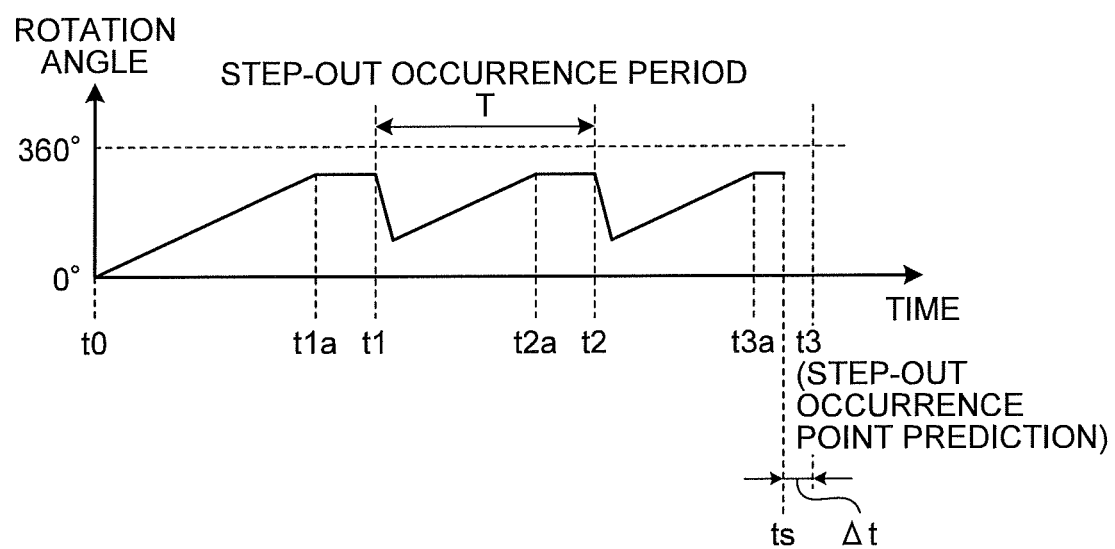
FIG. 10 is a diagram illustrating a relationship between the detected inverse rotation occurrence point and the next predictable inverse rotation occurrence point in the capsule medical apparatus system illustrated in FIG. 1.

When two-time inverse rotation occurrence points t1 and t2 are detected by the step-out generation detecting unit 34, the step-out generation prediction unit 35 obtains a step-out occurrence period T that is a time interval between the inverse rotation occurrence points t1 and t2 as illustrated in FIG. 10, and predicts an inverse rotation occurrence point t3 in the next step-out operation that is generated when the rotation of the rotating magnetic field Rf is continued at a constant rotating speed on the basis of the step-out occurrence period T.

When the inverse rotation occurrence point t3 in the predicted next step-out operation is obtained, the magnetic-field control instructing unit 36 outputs an instruction of stopping the generation of the rotating magnetic field Rf to the magnetic field control unit 8 just before the inverse rotation occurrence point t3. The magnetic field control unit 8 receives the instruction, and controls the power supply unit 9 to stop the magnetic-field generation performed by the magnetic field generating unit 2. In this way, the capsule endoscope 10 maintains a state where the needle 16 is surely and stably punctured into the luminal surface S without inverse rotation. Therefore, the liquid medicine Lq is surely injected into the affected part 21 by discharging the liquid medicine Lq from the needle 16 in the punctured state.

In this case, a time point just before the inverse rotation occurrence point t3 in the next step-out operation is a time point ts prior to the inverse rotation occurrence point t3 by a predetermined time Δt. The time point ts is set in a time period from a rotation stop point t3a, at which the rotation of the capsule endoscope 10 to the rotation direction of the rotating magnetic field Rf is stopped, to a time point before arriving at the inverse rotation occurrence point t3. The capsule endoscope 10 is in a state where a rotation is stopped during the time period.

Figure 11:
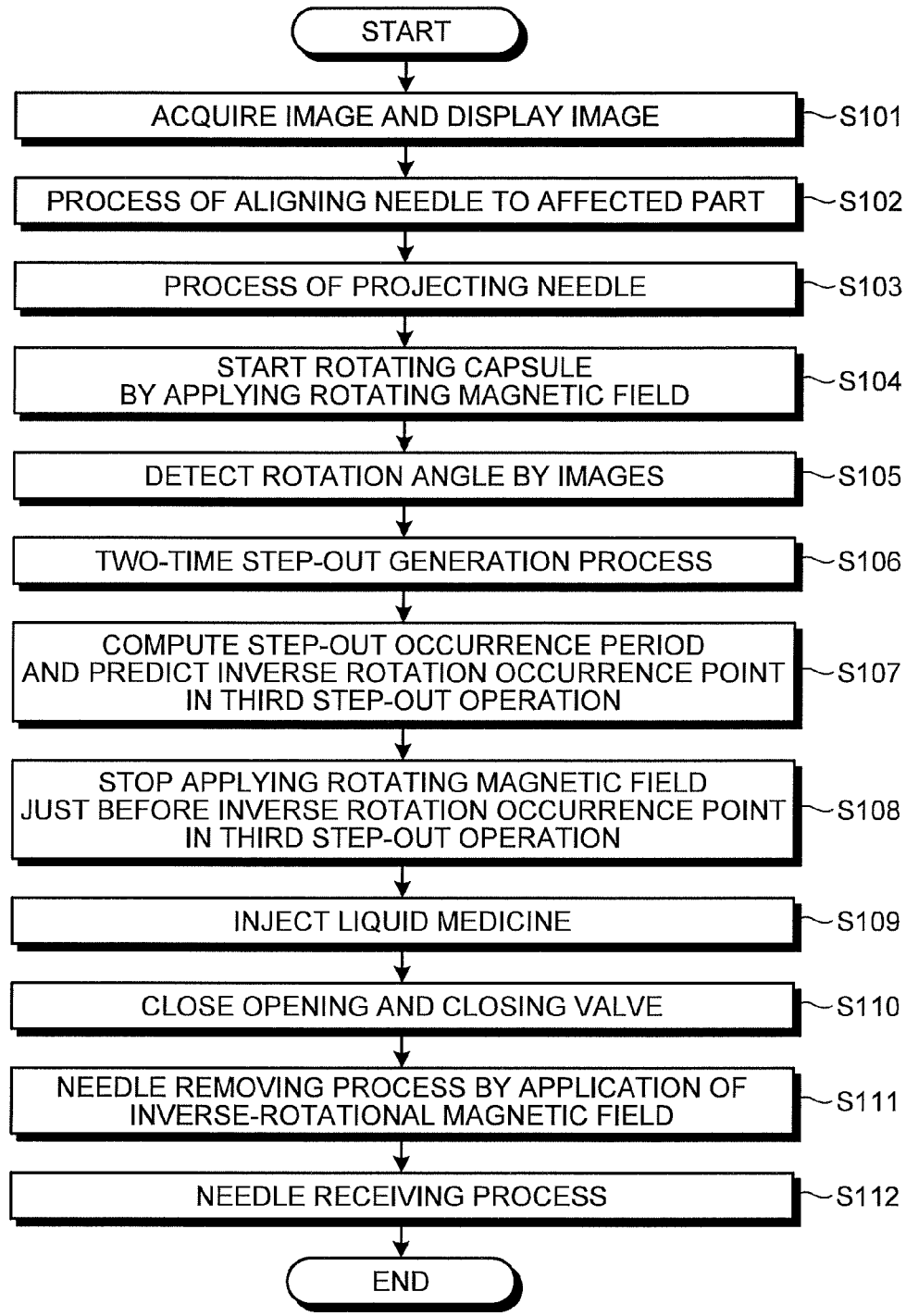
FIG. 11 is a flowchart illustrating a rotation puncture control process that is performed by the external control unit in the capsule medical apparatus system illustrated in FIG. 1.
Figure 12:
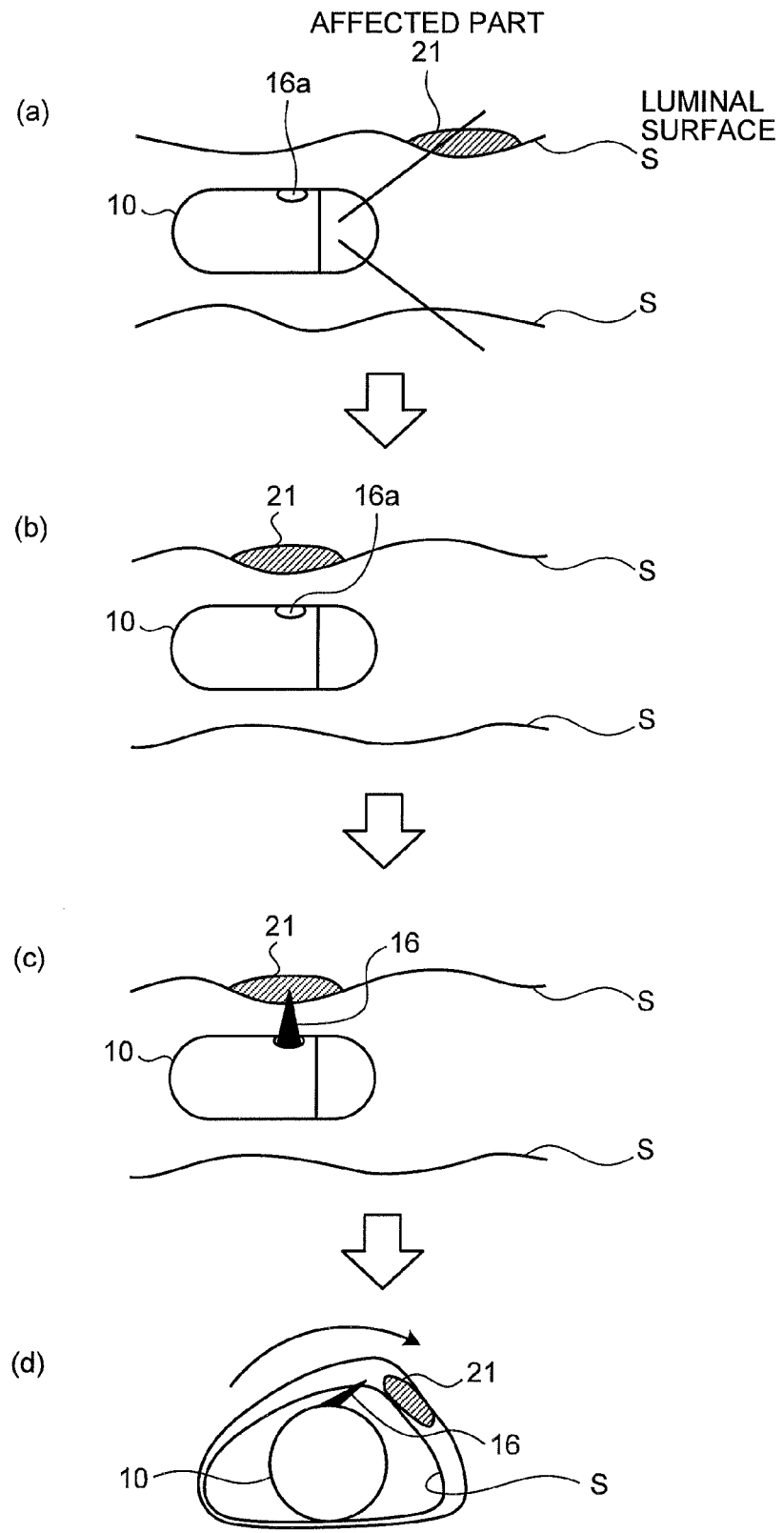
FIG. 12 is a pattern diagram illustrating the brief of a process from inside-body observation to liquid-medicine injection in the capsule medical apparatus system illustrated in FIG. 1.

Now, it will be explained about a liquid-medicine injection processing procedure with reference to the flowchart illustrated in FIGS. 11 and 12. In FIG. 11, the capsule medical apparatus system first makes the capsule endoscope 10 introduced into the living body acquire in-vivo images (FIG. 12(a)), and makes the transmitting and receiving unit 3 receive the acquired in-vivo images and makes the display unit 5 display the images to observe the inside of body cavity (Step S101). In addition, the capsule endoscope 10 acquires and transmits in-vivo images at a constant frame rate also continuously after that. After that, while the operator observes the intra-body-cavity images, the operator inputs manipulation information for aligning the needle 16 or the opening part 16a to the affected part 21 through the input unit 6 when the operator finds the affected part 21. When the manipulation information is input, the external control unit 4 performs a process (FIG. 12(b)) for aligning the needle 16 or the opening part 16a to the affected part 21 (Step S102).

After that, the external control unit 4 sends an instruction of projecting the needle 16 to the outside to the capsule endoscope 10. The capsule endoscope 10 receives the instruction, and drives the linear actuator 15 to project the needle 16 (Step S103, FIG. 12(c)). After that, the external control unit 4 controls the magnetic field generating unit 2 via the magnetic field control unit 8, and thus makes the magnetic field generating unit 2 generate the rotating magnetic field Rf for rotating the capsule endoscope 10 at a constant rate and makes the magnetic field generating unit 2 apply the rotating magnetic field Rf to the capsule endoscope 10 (Step S104, FIG. 12(d)). The capsule endoscope 10 starts its rotation by applying the rotating magnetic field Rf.

After that, the external control unit 4 detects the rotation angle of the capsule endoscope 10 on the basis of the in-vivo images that are sequentially received (Step S105). Moreover, the external control unit 4 continues to apply the rotating magnetic field Rf and generates at least two-time step-outs even if the generation of a step-out operation is detected (Step S106). Furthermore, the external control unit 4 computes the step-out occurrence period T and predicts the inverse rotation occurrence point of the capsule endoscope 10 in a step-out operation to be next generated, on the basis of the inverse rotation occurrence points of the capsule endoscope 10 in the plurality of detected step-out operations (Step S107).

After that, the external control unit 4 controls the magnetic field generating unit 2 to stop applying the rotating magnetic field Rf immediately before the inverse rotation occurrence point of the capsule endoscope 10 in the next step-out operation (Step S108), and makes the capsule endoscope 10 inject liquid medicine into the affected part 21 in a state where the needle 16 is stably punctured (Step S109). After that, the external control unit 4 makes the capsule endoscope 10 close the opening and closing valve 14 (Step S110), controls the magnetic field generating unit 2 to make the capsule endoscope 10 apply an inverse-rotational magnetic field and perform a process for removing the needle 16 (Step S111), further makes the capsule endoscope 10 perform a process for receiving the needle 16 (Step S112), and terminates the process. In this case, the removal process of the needle 16 may be performed by further applying a positive-rotational magnetic field to make the capsule endoscope 10 perform a step-out operation without applying an inverse-rotational magnetic field.

Moreover, the stop of application of a rotating magnetic field performed at Step S108 is autonomously performed by the external control unit 4. However, the present invention is not limited to this. The external control unit 4 may display the effect that the punctured state is stable on the display unit 5, and may stop the application of the rotating magnetic field on the basis of the manipulated signal input from the operator via the input unit 6.

In the first embodiment, when the capsule endoscope 10 is rotated inside the living body to perform the puncture of the needle 16, the puncture is stably performed in such a manner that the inverse-rotational operation does not occur on the basis of the inverse-rotational operation of the capsule endoscope 10. Therefore, even if the rotation of the capsule endoscope 10 cannot be directly observed, the puncture of the needle 16 can be surely and stably performed. Consequently, liquid medicine can be surely injected into the affected part 21.

Second Embodiment

Next, it will be explained about the second embodiment of the present invention. In the first embodiment, the rotation angle detecting unit 33 detects the rotation of the capsule endoscope 10 on the basis of the in-vivo images acquired by the capsule endoscope 10. However, in the second embodiment, the rotation of the capsule endoscope 10 can be directly detected from the outside.

Figure 13:
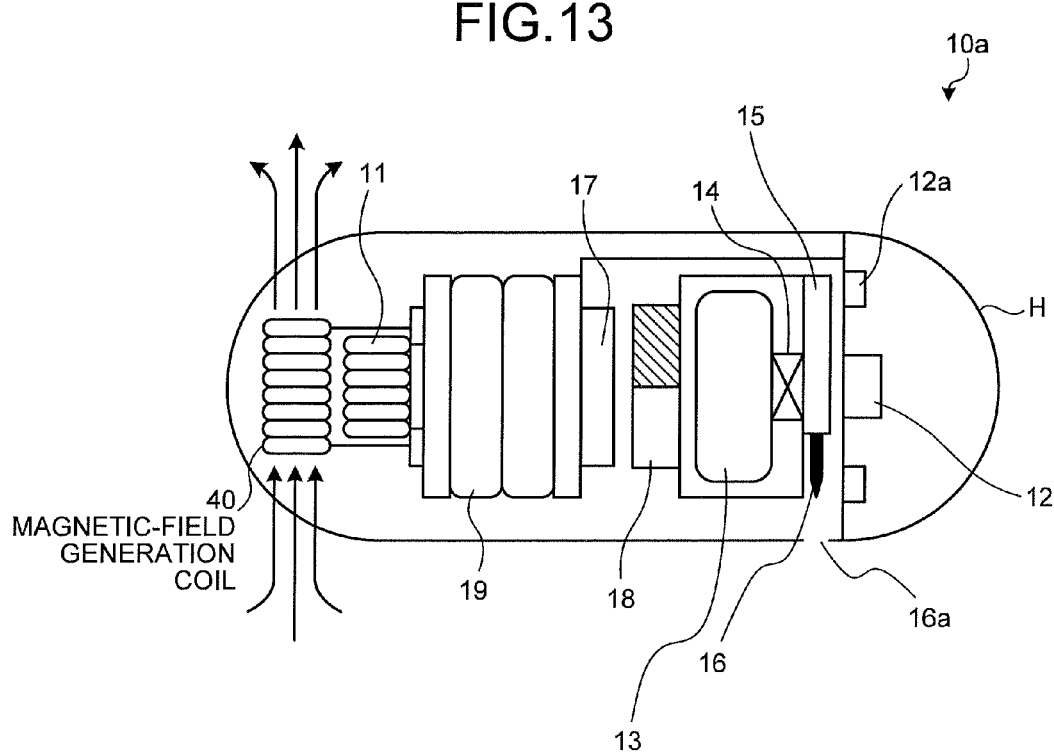
FIG. 13 is a sectional schematic view illustrating the configuration of a capsule endoscope according to a second embodiment of the present invention.

FIG. 13 is a sectional schematic view illustrating the configuration of a capsule endoscope 10a that is used in a capsule medical apparatus system according to the second embodiment of the present invention. As illustrated in FIG. 13, the capsule endoscope 10a includes a magnetic field emitting unit that emits a magnetic field toward the direction of the outside, specifically, a magnetic-field generation coil 40 that generates a magnetic field in a radial direction of the capsule endoscope 10a. The other configuration is the same as that of the capsule endoscope 10 and the same components have the same reference numbers.

Figure 14:
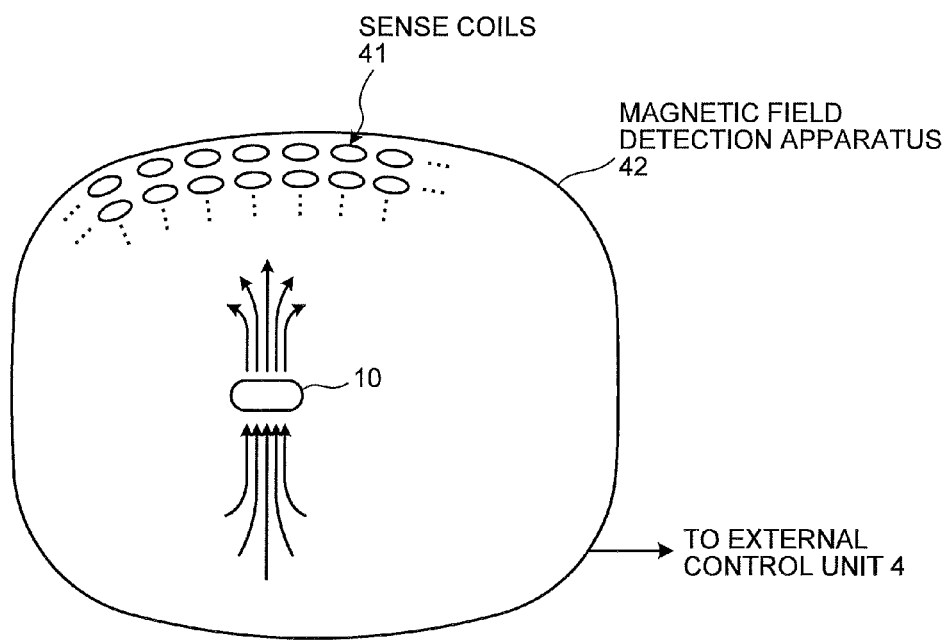
FIG. 14 is a pattern diagram illustrating the brief configuration of a magnetic field detection apparatus used when the capsule endoscope illustrated in FIG. 13 is used.

On the other hand, in the second embodiment, as illustrated in FIG. 14, similarly to the magnetic field generating unit 2, the capsule medical apparatus system includes a magnetic field detection apparatus 42 that is provided with a plurality of sense coil groups 41 for detecting a magnetic field to cover the capsule endoscope 10a from the outside of the capsule endoscope 10a. The sense coil groups 41 function as a magnetic field detecting unit that detects the magnetic field emitted from the magnetic field emitting unit of the capsule endoscope 10a, that is, the magnetic field emitted from the magnetic-field generation coil 40. The magnetic field detection apparatus 42 transmits magnetic-field intensity detected by the sense coil groups 41 to the external control unit 4.

When the magnetic field generating unit 2 generates a rotating magnetic field to rotate the capsule endoscope 10a, the magnetic-field generation coil 40 is applied with an electric current and generates a magnetic field under the control of the control unit 17. Because the generated magnetic field is rotated along with the rotation of the capsule endoscope 10a and further has directivity, the external control unit 4 can detect the rotation angle of the capsule endoscope 10a on the basis of the magnetic-field intensity detected by the sense coil groups 41.

Figure 15:
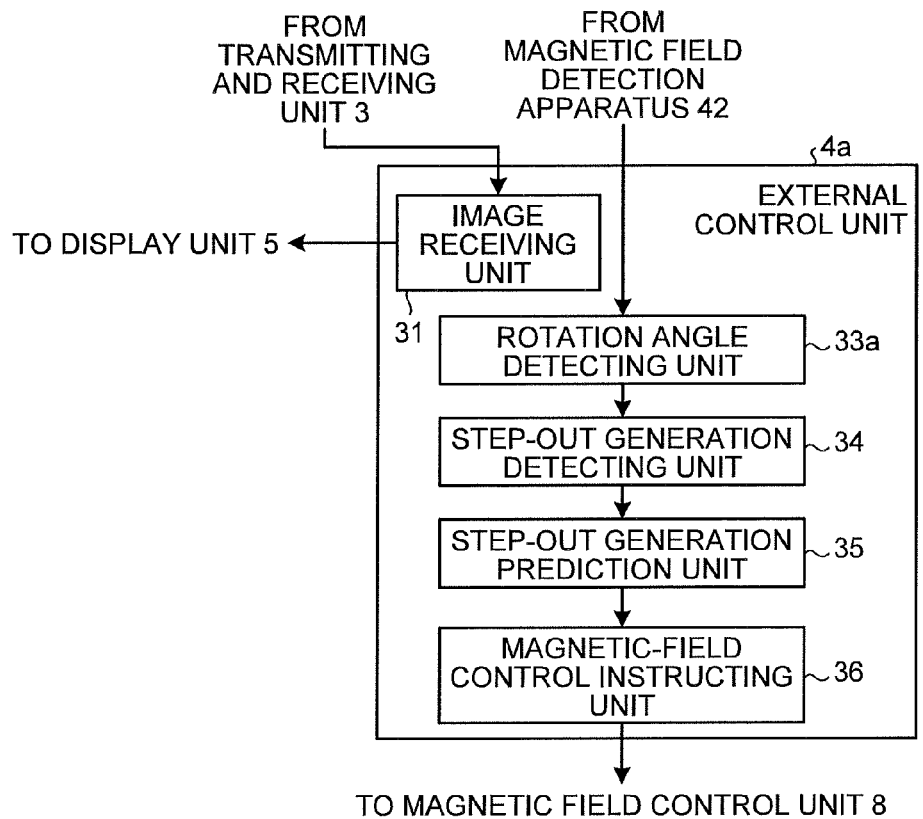
FIG. 15 is a block diagram illustrating the configuration of an external control unit according to the second embodiment of the present invention.

In this case, as illustrated in FIG. 15, an external control unit 4a corresponding to the external control unit 4 can delete the image comparing unit 32 because it is not necessary to perform image processing for detecting a rotation angle. Moreover, instead of the rotation angle detecting unit 33 according to the first embodiment, a rotation angle detecting unit 33a that detects a rotation state, specifically, a rotation angle of the capsule endoscope 10a on the basis of the magnetic-field intensity detected by the sense coil groups 41 is provided as a rotation detecting unit or a rotation detecting means. When a function for detecting the position, direction, and rotation angle of the capsule endoscope 10a and the position of the affected part 21 is given to the capsule medical apparatus system in such a manner that the needle 16 of the capsule endoscope 10a and the affected part 21 can be aligned without observing intra-body-cavity images, the image receiving unit 31 can be deleted from the external control unit 4a.

The position and posture of the capsule endoscope 10a can be detected with high precision and the guidance of the capsule endoscope 10a can be performed with high precision by using the magnetic field detection apparatus 42.

Third Embodiment

Next, it will be explained about the third embodiment of the present invention. In the first embodiment described above, the rotation angle detecting unit 33 detects the rotation of the capsule endoscope 10 on the basis of the in-vivo images acquired by the capsule endoscope 10. In the third embodiment, the capsule endoscope 10 directly detects the rotation of the capsule endoscope 10 and transmits the rotation information.

Figure 16:
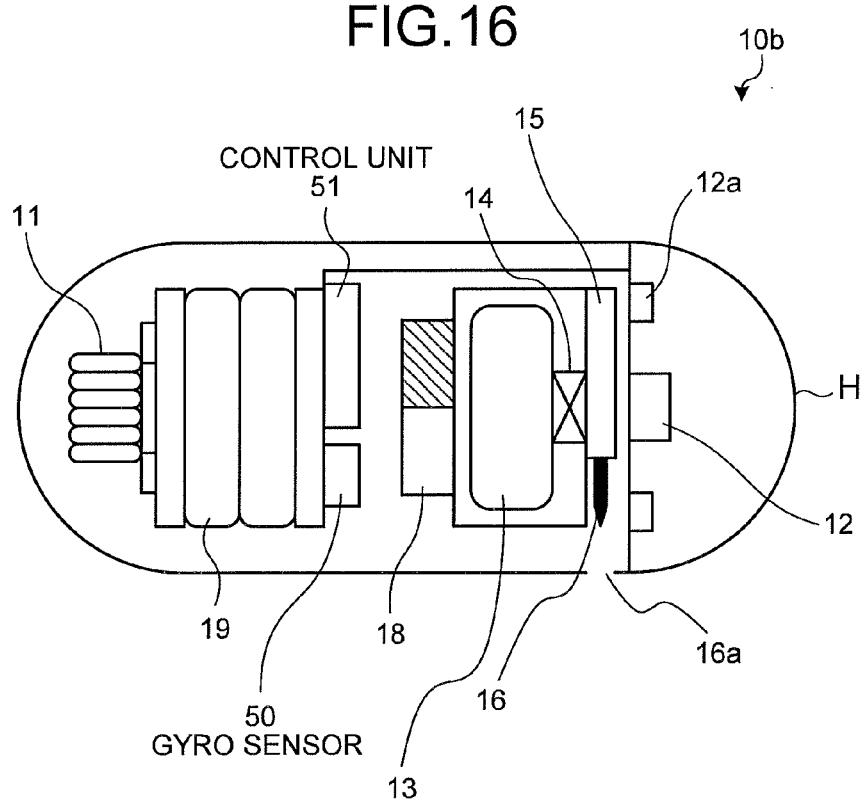
FIG. 16 is a sectional schematic view illustrating the configuration of a capsule endoscope according to a third embodiment of the present invention.

FIG. 16 is a sectional schematic view illustrating the configuration of a capsule endoscope 10b that is used in a capsule medical apparatus system according to the third embodiment of the present invention. As illustrated in FIG. 13, the capsule endoscope 10b includes a gyro sensor 50 that detects a rotation angle of the capsule endoscope 10b. The gyro sensor 50 functions as a rotation angle detecting unit or a rotation angle detecting means. Moreover, a control unit 51 corresponding to the control unit 17 performs a control for transmitting the rotation angle acquired by the gyro sensor 50 to the outside. The other configuration is the same as that of the capsule endoscope 10 and the same components have the same reference numbers.

Figure 17:
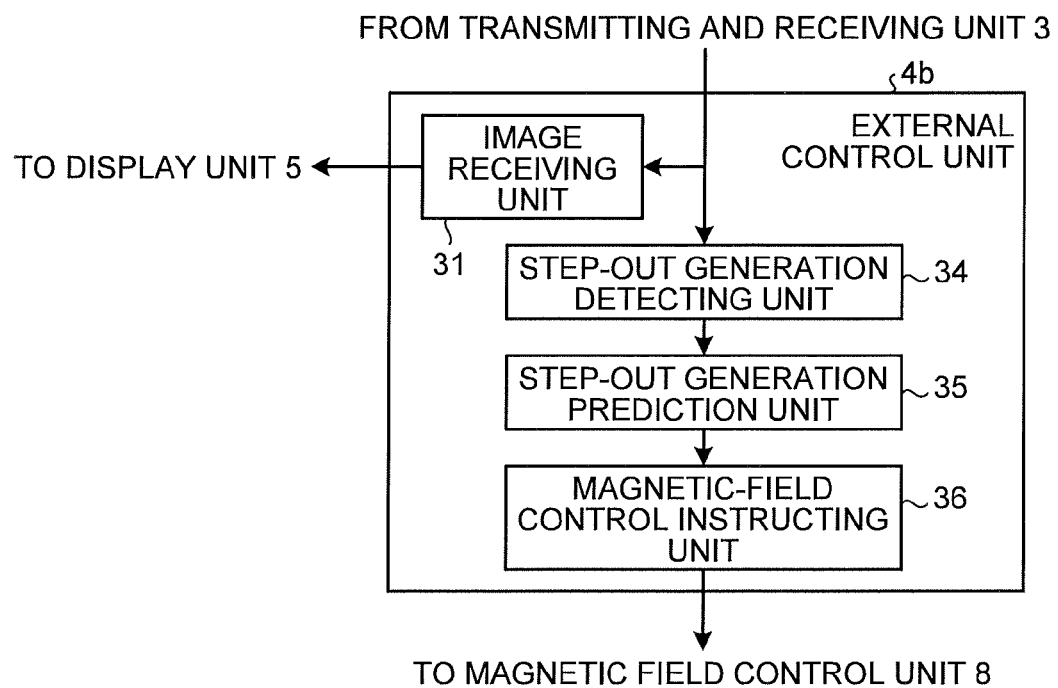
FIG. 17 is a block diagram illustrating the configuration of an external control unit according to the third embodiment of the present invention.

In this case, as illustrated in FIG. 17, because an external control unit 4b corresponding to the external control unit 4 does not perform image processing and rotation angle detection process for detecting a rotation angle, the image comparing unit 32 and the rotation angle detecting unit 33 can be omitted. Moreover, when a function for detecting the position, direction, and rotation angle of the capsule endoscope 10b and the position of the affected part 21 is given to the capsule medical apparatus system in such manner that the needle 16 of the capsule endoscope 10b and the affected part 21 can be aligned without observing intra-body-cavity images, the image receiving unit 31 can be omitted from the external control unit 4b.

In the third embodiment, because the gyro sensor 50 directly detects the rotation angle of the capsule endoscope 10b and thus time lag accompanied with the rotation angle detection process does not occur, the rotation angle of the capsule endoscope 10b can be grasped in substantially real time.

Fourth Embodiment

Next, it will be explained about the fourth embodiment of the present invention. In any of the first to third embodiments described above, the step-out generation detecting unit 34 detects the generation of a step-out operation on the basis of the rotation angles of the capsule endoscopes 10, 10a, and 10b. In the fourth embodiment, the step-out generation detecting unit detects the generation of a step-out operation on the basis of the rotating speed of the capsule endoscope.

Figure 18:
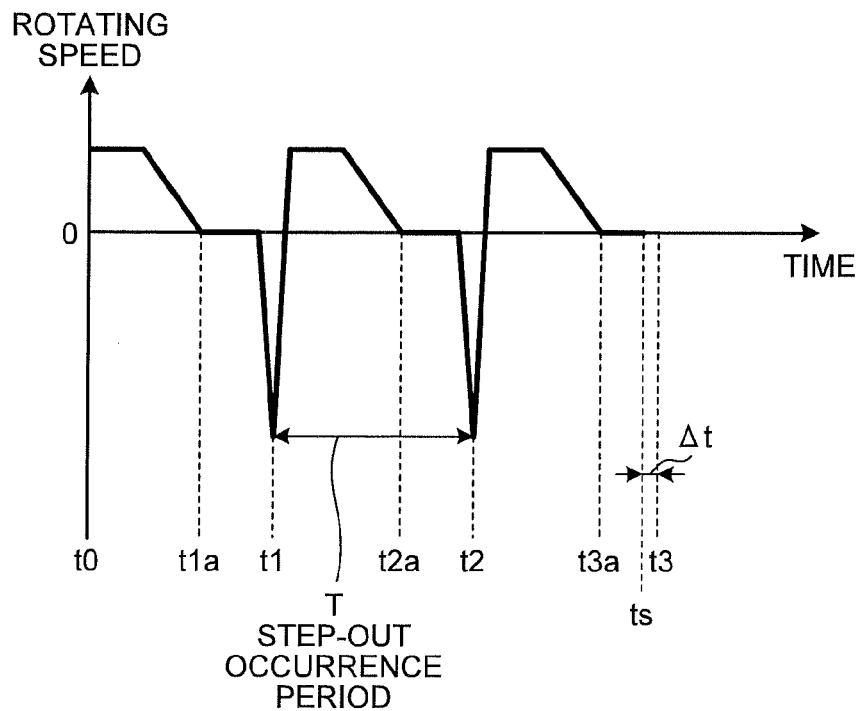
FIG. 18 is a diagram illustrating the time change of a rotating speed of a capsule endoscope according to a fourth embodiment of the present invention.

In the fourth embodiment, the gyro sensor 50 of the capsule endoscope 10b illustrated in FIG. 16 directly detects a rotating speed instead of the rotation angle of the capsule endoscope 10b, and the step-out generation detecting unit detects the generation of a step-out operation on the basis of the change of the rotating speed. The gyro sensor 50 functions as a rotating speed detecting unit or a rotating speed detecting means that detects a rotating speed of the capsule endoscope 10b. When the capsule endoscope 10b is rotated in synchronization with a rotating magnetic field without the step-out operation, the rotating speed of the capsule endoscope 10b has a constant value. On the contrary, when the step-out operation occurs, the temporal change of a rotating speed as illustrated in FIG. 18 occurs periodically. The temporal change of the rotating speed corresponds to the temporal change of a rotation angle illustrated in FIG. 9. A rotating speed is a value that is obtained by differentiating a rotation angle with respect to time.

In other words, in the case of the first application of a rotating magnetic field, the rotation of the capsule endoscope 10b is synchronized with the rotation of the rotating magnetic field from a time point t0 and a rotating speed is constant. However, after that, the rotating speed gradually decreases due to a reaction force from the luminal surface S, the rotating speed becomes zero at a time point t1a, and the capsule endoscope 10b is stopped. After that, the rotating magnetic field continues to be applied and is inversely rotated suddenly at a time point t1 to indicate a large negative rotating speed. After that, the capsule endoscope 10b is again returned to a rotating speed that is synchronized with the rotating magnetic field to repeat the above time change.

Even if the rotating speed is detected, as illustrated in FIG. 18, inverse rotation occurrence points t1 and t2 at which the rotating speed is suddenly changed can be detected, and thus a step-out occurrence period T can be easily obtained by the inverse rotation occurrence points t1 and t1 and the next inverse rotation occurrence point t3 can be easily predicted. In this case, because the rotating speed of the inverse rotation occurrence point is sharply changed, an inverse rotation occurrence point can be easily detected by the step-out generation detecting unit.

Figure 19:
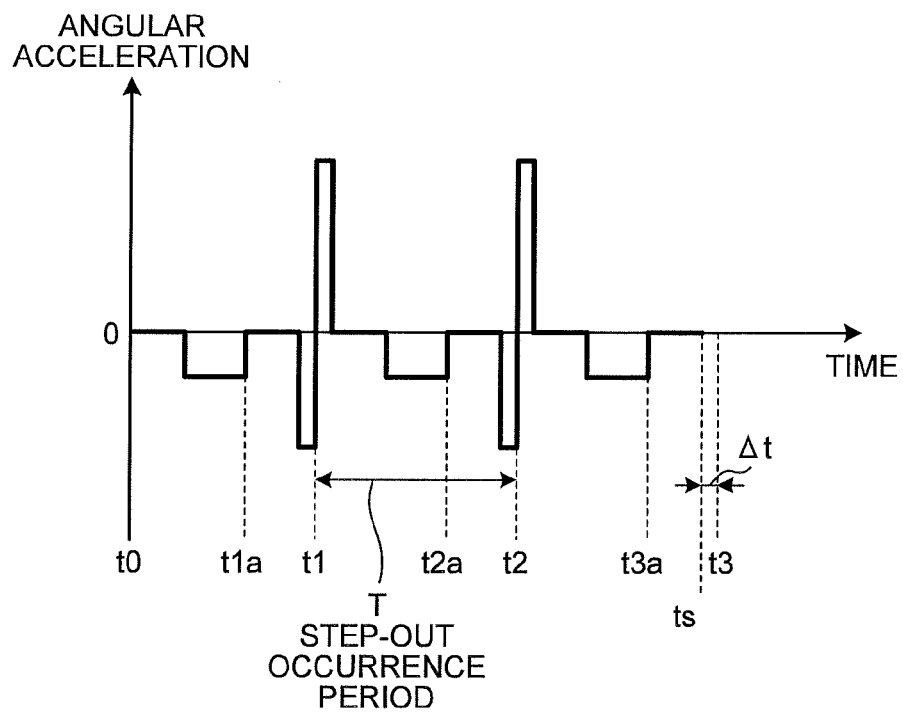
FIG. 19 is a diagram illustrating the time change of a rotating speed of a capsule endoscope according to an alternative example of the fourth embodiment of the present invention.

The gyro sensor 50 may detect an angular acceleration instead of a rotation angle, and the step-out generation detecting unit may detect the generation of a step-out operation on the basis of the change of the angular acceleration. The gyro sensor 50 functions as an angular acceleration detecting unit or an angular acceleration detecting means that detects an angular acceleration of the capsule endoscope 10b. In this case, the angular acceleration of the capsule endoscope 10b indicates a temporal change as illustrated in FIG. 19. Also in this case, because the angular acceleration is sharply changed at the inverse rotation occurrence points t1 and t2, the step-out generation detecting unit can easily detect an inverse rotation occurrence point. In addition, when an angular acceleration is secondary time derivative of an angle, an inverse rotation occurrence point is a zero-cross point of an angular acceleration. For this reason, an inverse rotation occurrence point can be detected more easily and with high precision.

In the fourth embodiment described above, a rotating speed or an angular acceleration is detected by the gyro sensor 50. However, the present invention is not limited to this. A rotating speed detecting unit may calculate a rotating speed by a primary time-derivative process on the basis of the detection result of a rotation angle based on the difference between images according to the first embodiment or the detection result of a rotation angle by the outside detection of a magnetic field according to the second embodiment. Alternatively, an angular acceleration detecting unit may calculate an angular acceleration by the secondary time-derivative process of a rotation angle or the primary time-derivative process of a rotating speed. The rotating speed detecting unit functions as a rotating speed detecting means and the angular acceleration detecting unit functions as an angular acceleration detecting means.

Figure 20:
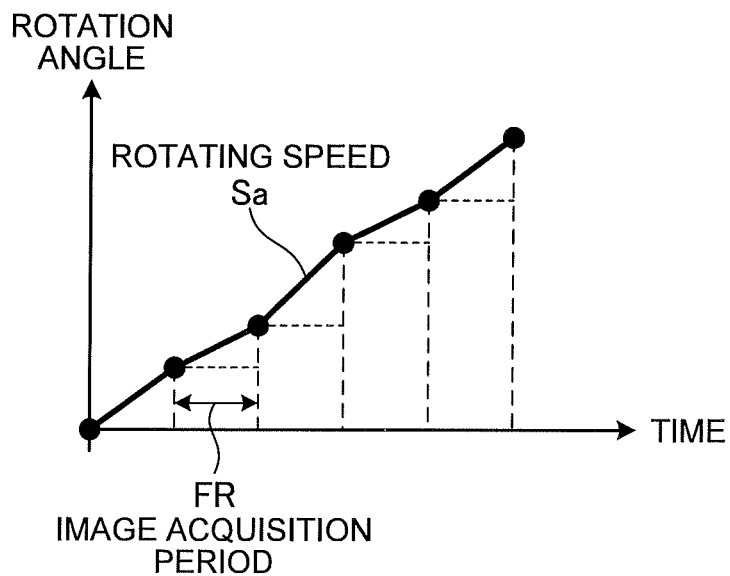
FIG. 20 is a diagram illustrating a processing matter of calculating a rotating speed by using a primary time-derivative process of the rotation angle on the basis of the time change of a rotation angle obtained from a difference between adjacent in-vivo images in time series in the capsule medical apparatus system of the present invention.

FIG. 20 is a diagram illustrating a processing matter in which the rotating speed detecting unit calculates a rotating speed by using a primary time-derivative process of a rotation angle on the basis of the time change of a rotation angle obtained from a difference between adjacent in-vivo images in time series. In this case, the acquired in-vivo images are captured at a constant frame rate, and the in-vivo images are output at a constant image acquisition period FR. The rotating speed detecting unit divides a rotation-angle difference between the obtained in-vivo images by the constant image acquisition period FR to calculate and output a rotating speed Sa.

Figure 21:
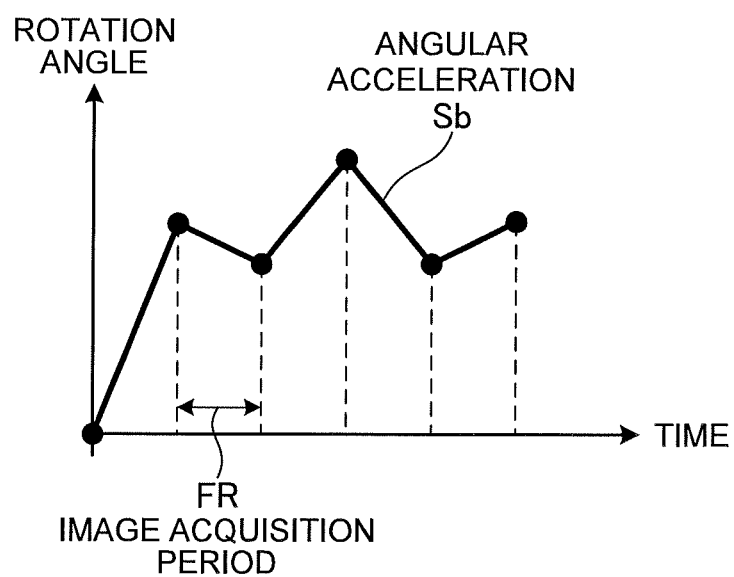
FIG. 21 is a diagram illustrating a processing matter of performing a primary time-derivative process of a rotating speed to calculate an angular acceleration on the basis of the time change of a rotating speed in the capsule medical apparatus system of the present invention.

FIG. 21 is a diagram illustrating a processing matter of performing a primary time-derivative process of a rotating speed to calculate an angular acceleration on the basis of the time change of the rotating speed. The angular acceleration detecting unit further differentiates the rotating speed obtained in FIG. 20 with respect to time to calculate and output an angular acceleration Sb. In this case, the acquisition of an angular acceleration from the rotation angle of an image requires the rotation angles of at least three or more adjacent images in time series.

Fifth Embodiment

Next, it will be explained about the fifth embodiment of the present invention. In any of the first to fourth embodiments described above, the step-out generation detecting unit 34 detects consecutive two or more inverse rotation occurrence points t1 and t2, the step-out generation prediction unit 35 predicts the next inverse rotation occurrence point t3, and the external control unit 4 stops applying a rotating magnetic field to the capsule endoscope by the magnetic field generating unit 2 just before the inverse rotation occurrence point t3. However, in the fifth embodiment, the application of a rotating magnetic field is stopped by one step-out operation.

In other words, the capsule endoscope is in a state where its rotation is stopped in time periods prior to the inverse rotation occurrence points t1 and t2. In the time periods of the state, that is, a time period from a rotation stop point t1a to the inverse rotation occurrence point t1 and a time period from a rotation stop point t2a to the inverse rotation occurrence point t2, a rotation angle is constant, a rotating speed is constant as zero, and an angular acceleration is constant as zero. Therefore, the rotation stop point t1a at which the rotation of the capsule endoscope is stopped can be detected. In the fifth embodiment, when the step-out generation detecting unit detects the rotation stop point t1a, the external control unit 4, specifically, the magnetic-field control instructing unit 36 outputs an instruction of stopping the application of a rotating magnetic field to the magnetic field control unit 8 at the rotation stop point t1a, similarly to the time point just before the inverse rotation occurrence point. In this way, a sure and stable punctured state can be obtained and a time for the puncture operation of a needle can be shortened, by the detection of only one rotation stop point.

Sixth Embodiment

Next, it will be explained about the sixth embodiment of the present invention. In the first to fifth embodiments described above, the application of a rotating magnetic field to the capsule endoscope is stopped just before the inverse rotation occurrence point t3 in the next step-out operation or at the rotation stop point t1a. However, in the sixth embodiment, the external control unit 4 only controls the magnetic field control unit 8 in such a manner that the rotation of a rotating magnetic field is stopped just before the inverse rotation occurrence point t3 in the next step-out operation or at the rotation stop point t1a, and thus the application of a magnetic field is maintained without stopping the application of the magnetic field to the capsule endoscope.

In the sixth embodiment, because the stopped state of the capsule endoscope can be positively maintained, the punctured state of a needle can be further stabilized.

Seventh Embodiment

Next, it will be explained about the seventh embodiment of the present invention. In the first to fifth embodiments described above, the application of a rotating magnetic field to the capsule endoscope is stopped just before the inverse rotation occurrence point t3 in the next step-out operation or at the rotation stop point t1a. However, in the seventh embodiment, the external control unit, specifically, the magnetic-field control instructing unit controls the magnetic field generating unit to lower the rotating speed of the rotating magnetic field to an extremely low speed just before the inverse rotation occurrence point t3 in the next step-out operation or from the rotation stop point t1a, and thus the punctured state of the needle of the capsule endoscope is substantially maintained.

Figure 22:
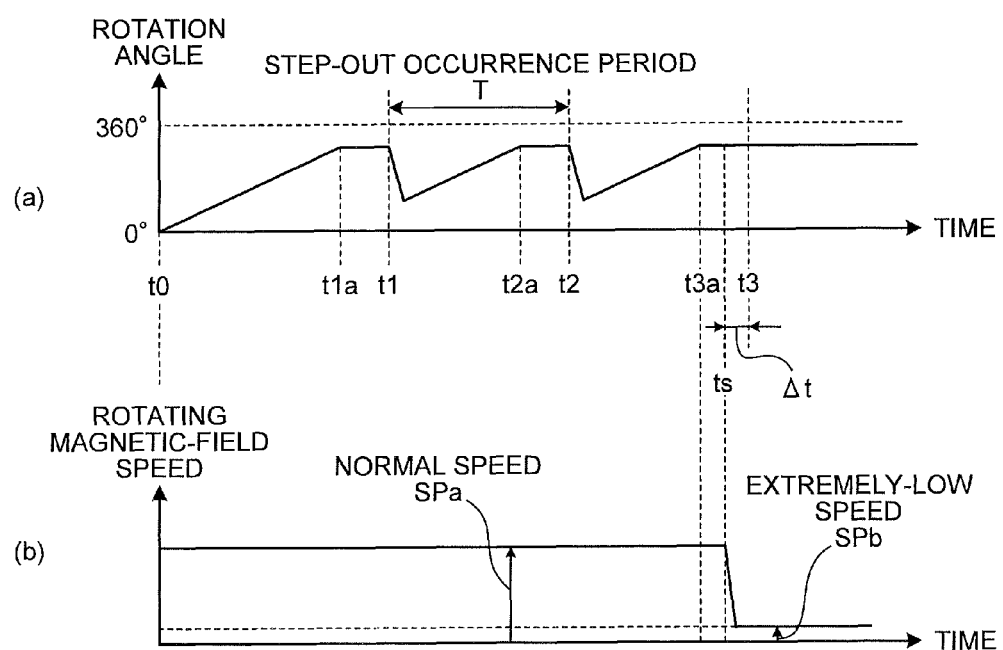
FIG. 22 is a diagram illustrating the time change of a rotating speed of a rotating magnetic field according to a seventh embodiment of the present invention.

FIG. 22 is a diagram illustrating the temporal change of the rotating speed of a rotating magnetic field according to the seventh embodiment. As is apparent from the comparison between the rotation angle of the capsule endoscope illustrated in (a) of FIG. 22 and the rotating speed (rotating magnetic-field speed) of the rotating magnetic field illustrated in (b) of FIG. 22, the external control unit 4 controls the magnetic field control unit 8 from the time point ts immediately before the inverse rotation occurrence point t3 in the next step-out operation, and then the magnetic field control unit 8 receives this and controls the magnetic field generating unit 2 to lower the rotating speed (rotating magnetic-field speed) of the external magnetic field (rotating magnetic field) Rf from the past rotating magnetic-field speed (normal speed) SPa to the extremely-low rotating magnetic-field speed SPb.

Figure 23A:
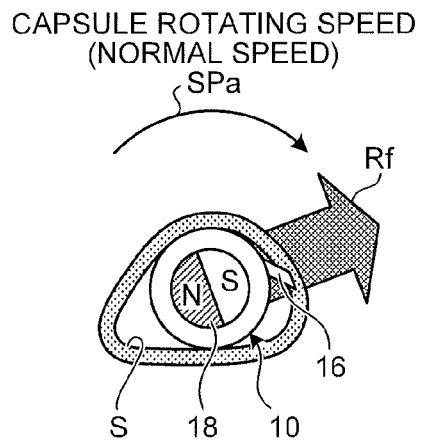
FIG. 23A is a conceptual diagram illustrating the rotating speed of the capsule endoscope from a time point t0 to a time point t3a illustrated in FIG. 22.
Figure 23B:
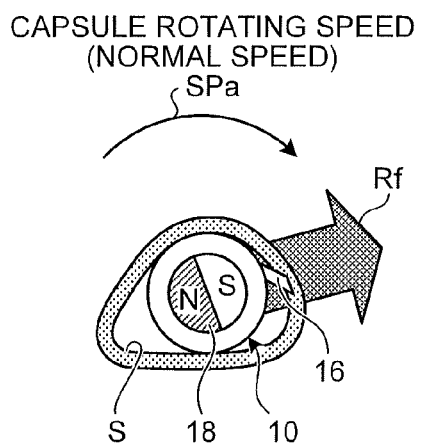
FIG. 23B is a conceptual diagram illustrating the rotating speed of the capsule endoscope from the time point t3a to a time point is illustrated in FIG. 22.
Figure 23C:
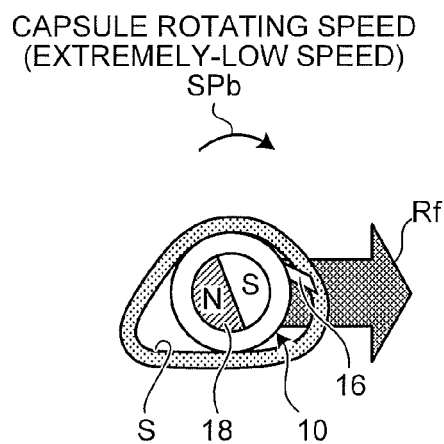
FIG. 23C is a conceptual diagram illustrating the rotating speed of the capsule endoscope at liquid-medicine injection performed after a time point t3 illustrated in FIG. 22.

The rotating speed of the rotating magnetic field Rf is set to the rotating magnetic-field speed SPa from the time point t0 to the time point ts illustrated in FIG. 22, and thus the rotating speed of the capsule endoscope also becomes SPa (FIGS. 23A and 23B). Moreover, the rotating speed of the rotating magnetic field Rf is reduced to be set to the rotating magnetic-field speed SPb before the time point t3 from the time point ts illustrated in FIG. 22, and thus the rotating speed of the capsule endoscope is also set to SPb (FIG. 23C) to extremely slowly rotate the capsule endoscope. In other words, a time required to arrive at the next inverse rotation occurrence point t3 is enlarged, and thus liquid medicine is injected into an affected part from the capsule endoscope before arriving at the inverse rotation occurrence point t3.

Even by the seventh embodiment, the stopped state of a capsule endoscope can be stably maintained and the punctured state of a needle can be stabilized.

Similarly to the fifth embodiment, the rotation of the capsule endoscope may be substantially stopped and thus the punctured state of a needle may be stabilized by suddenly setting the rotation speed as the extremely-low rotating magnetic-field speed SPb from the rotation stop point t1a in the first step-out operation.

According to the embodiments explained above, when the needle of the capsule medical apparatus is diagonally projected and punctured with respect to a luminal surface, because the step-out operation detecting means detects the step-out operation of the capsule medical apparatus and the magnetic field control means controls the rotating magnetic field generation apparatus on the basis of the detection result performed by the step-out operation detecting means, the puncture of the needle can be surely performed by rotating the capsule medical apparatus by using the outside rotating magnetic field.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical apparatus system comprising:
a rotating magnetic field generation apparatus that generates a desired rotating magnetic field in three-dimensional directions;
a capsule medical apparatus that is introduced into a living body, includes a magnet and a needle with which the capsule medical apparatus punctures a luminal surface by diagonally projecting and retracting the needle in a rotation direction of the rotating magnetic field that is perpendicular to a center of a longitudinal axis of a casing of the capsule medical apparatus, and rotates in a direction of the rotating magnetic field when the rotating magnetic field is applied to the magnet, wherein in a diagonally projected state the needle is inclined to an outside of the capsule medical apparatus with respect to a tangent line of the casing in such a manner that a leading end of the needle is turned along the rotation direction around a center of the longitudinal axis of the casing;
a step-out operation detecting unit that detects, when the needle is diagonally projected toward the luminal surface to puncture the luminal surface, a step-out operation by which the capsule medical apparatus is inversely rotated at a rotating speed larger than a rotating speed of the rotating magnetic field after rotation of the capsule medical apparatus in the rotation direction of the rotating magnetic field is stopped; and
a magnetic-field control unit that controls the rotating magnetic field generation apparatus on the basis of a detection result performed by the step-out operation detecting unit.

2. The capsule medical apparatus system according to claim 1, further comprising a step-out predicting unit that predicts an inverse rotation occurrence point in a next step-out operation of the capsule medical apparatus on the basis of the detection result performed by the step-out operation detecting unit,
wherein the magnetic-field control unit controls the rotating magnetic field generation apparatus before a predetermined time of the inverse rotation occurrence point on the basis of the inverse rotation occurrence point in the next step-out operation predicted by the step-out predicting unit.

3. The capsule medical apparatus system according to claim 2, wherein the magnetic-field control unit controls the rotating magnetic field generation apparatus to stop generating a magnetic field before the predetermined time of the inverse rotation occurrence point in the next step-out operation.

4. The capsule medical apparatus system according to claim 2, wherein the magnetic-field control unit controls the rotating magnetic field generation apparatus to stop rotating a magnetic field before the predetermined time of the inverse rotation occurrence point in the next step-out operation.

5. The capsule medical apparatus system according to claim 2, wherein the magnetic-field control unit controls the rotating magnetic field generation apparatus to reduce the rotating speed of the rotating magnetic field before the predetermined time of the inverse rotation occurrence point in the next step-out operation.

6. The capsule medical apparatus system according to claim 2, wherein
   the step-out operation detecting unit detects a rotation stop point at which a rotation of the capsule medical apparatus is stopped before the inverse rotation occurrence point,
   the step-out predicting unit predicts a rotation stop point before the inverse rotation occurrence point in the next step-out operation of the capsule medical apparatus on the basis of the detection result performed by the step-out operation detecting unit, and
   the magnetic-field control unit defines the predetermined time as an interval from the inverse rotation occurrence point in the next step-out operation to a next rotation stop point.

7. The capsule medical apparatus system according to claim 2, wherein
   the rotating speed of the rotating magnetic field is constant, and
   the step-out predicting unit obtains a step-out occurrence period between the inverse rotation occurrence points in two-time or more adjacent step-out operations detected by the step-out operation detecting unit and predicts an inverse rotation occurrence point in a next step-out operation of the capsule medical apparatus on the basis of the step-out occurrence period.

8. The capsule medical apparatus system according to claim 2, further comprising a rotation angle detecting unit that detects a rotation angle of the capsule medical apparatus,
   wherein the step-out operation detecting unit detects the step-out operation on the basis of a change of the rotation angle of the capsule medical apparatus detected by the rotation angle detecting unit.

9. The capsule medical apparatus system according to claim 8, wherein
   the capsule medical apparatus further includes an image acquiring unit that sequentially acquires in-vivo images, and
   the rotation angle detecting unit detects the rotation angle of the capsule medical apparatus on the basis of a difference between the adjacent in-vivo images in time series that are sequentially outputted from the image acquiring unit.

10. The capsule medical apparatus system according to claim 2, further comprising a rotating speed detecting unit that detects a rotating speed of the capsule medical apparatus,
    wherein the step-out operation detecting unit detects the step-out operation on the basis of a change of the rotating speed of the capsule medical apparatus detected by the rotating speed detecting unit.

11. The capsule medical apparatus system according to claim 10, wherein
    the capsule medical apparatus further includes an image acquiring unit that sequentially acquires in-vivo images, and
    the rotating speed detecting unit detects the rotating speed of the capsule medical apparatus on the basis of a difference between the adjacent in-vivo images in time series that are sequentially outputted from the image acquiring unit.

12. The capsule medical apparatus system according to claim 2, further comprising an angular acceleration detecting unit that detects an angular acceleration of the capsule medical apparatus,
    wherein the step-out operation detecting unit detects the step-out operation on the basis of a change of the angular acceleration of the capsule medical apparatus detected by the angular acceleration detecting unit.

13. The capsule medical apparatus system according to claim 12, wherein
    the capsule medical apparatus further includes an image acquiring unit that sequentially acquires in-vivo images, and
    the angular acceleration detecting unit detects the angular acceleration of the capsule medical apparatus on the basis of a difference between three adjacent in-vivo images in time series that are sequentially outputted from the image acquiring unit.

14. The capsule medical apparatus system according to claim 2, further comprising:
    a magnetic field emitting unit that is provided in the capsule medical apparatus and emits a magnetic field from the capsule medical apparatus to an external direction;
    a magnetic field detecting unit that is provided around an outside of the capsule medical apparatus and detects the magnetic field emitted from the magnetic field emitting unit; and
    a rotation detecting unit that detects a rotation state of the capsule medical apparatus on the basis of the magnetic field detected by the magnetic field detecting unit,
    wherein the step-out operation detecting unit detects the step-out operation on the basis of the rotation state of the capsule medical apparatus detected by the rotation detecting unit.

15. The capsule medical apparatus system according to claim 1, wherein the magnetic-field control unit controls the rotating magnetic field generation apparatus in response to which the step-out operation detecting unit detects a stop of rotation before inversely rotating the capsule medical apparatus.

* * * * *